US011382745B2

(12) United States Patent
Faurie (10) Patent No.: US 11,382,745 B2
(45) Date of Patent: Jul. 12, 2022

(54) ASSEMBLY FOR REPLACING A HEART VALVE OR A CORONARY ANGIOPLASTY ASSEMBLY (71) Applicant: ELECTRODUCER, Meylan (FR)

(72) Inventor: Benjamin Faurie, Meylan (FR)

(73) Assignee: ELECTRODUCER, Meylan (FR)

( * ) Notice: Subject to any disclaimer, the term of this patent is extended or adjusted under 35 U.S.C. 154(b) by 117 days.

(21) Appl. No.: 16/339,575

(22) PCT Filed: Oct. 5, 2017

(86) PCT No.: PCT/EP2017/075362
§ 371 (c)(1),
(2) Date: Apr. 4, 2019

(87) PCT Pub. No.: WO2018/065523
PCT Pub. Date: Apr. 12, 2018

(65) Prior Publication Data
US 2019/0224011 A1 Jul. 25, 2019

(30) Foreign Application Priority Data

Oct. 7, 2016 (FR) ...................................... 1659669
Oct. 7, 2016 (FR) ...................................... 1659671
Oct. 7, 2016 (FR) ...................................... 1659673

(51) Int. Cl.
A61F 2/24 (2006.01)
A61N 1/05 (2006.01)
(Continued)

(52) U.S. Cl.
CPC ........ *A61F 2/2436* (2013.01); *A61B 17/3468* (2013.01); *A61B 18/16* (2013.01);
(Continued)

(58) Field of Classification Search
CPC ...... A61F 2/2427; A61F 2/243; A61F 2/2433; A61F 2/2436; A61F 2/2439;
(Continued)

(56) References Cited

U.S. PATENT DOCUMENTS 3,893,461 A 7/1975 Preston
4,541,140 A 9/1985 Parsonnet
(Continued)

FOREIGN PATENT DOCUMENTS

WO 93/01768 A1 2/1993
WO 95/20360 A1 8/1995
(Continued)

OTHER PUBLICATIONS

International Search Report for Corresponding International Application No. PCT/EP2017/075362 dated Dec. 12, 2017.
(Continued)

*Primary Examiner* — Katherine H Schwiker
*Assistant Examiner* — Raihan R Khandker
(74) *Attorney, Agent, or Firm* — Pearne & Gordon LLP (57) ABSTRACT The present invention relates to an assembly for replacing a heart valve or to a coronary angioplasty assembly, comprising an introduction sheath (13) for an introducer (1) or for a delivery catheter (1'), which is smaller compared to an introducer, intended to be introduced into an artery of a human body. The invention basically comprises: either integrating the metal support of an electrode of the cardiac stimulator into a part to be fitted around the introduction sheath that is introduced into the artery of a patient or into a guide wire that becomes a bipolar electrode support; or connecting the cathode of an external cardiac stimulator to the guide wire of an artificial valve and the anode to a transcutaneous electrode in contact with the skin of the patient.

7 Claims, 7 Drawing Sheets (51) Int. Cl.
*A61N 1/36* (2006.01)
*A61B 17/00* (2006.01)
*A61B 17/34* (2006.01)
*A61B 18/16* (2006.01)
*A61B 17/22* (2006.01)

(52) U.S. Cl.
CPC ......... *A61N 1/056* (2013.01); *A61N 1/36014* (2013.01); *A61B 2017/00044* (2013.01); *A61B 2017/00243* (2013.01); *A61B 2017/22097* (2013.01); *A61B 2017/22098* (2013.01); *A61F 2/2418* (2013.01)

(58) Field of Classification Search
CPC ........ A61F 2/2418; A61B 2017/00243; A61N 1/056; A61M 2025/09091; A61M 2025/09133
See application file for complete search history.

(56) References Cited

U.S. PATENT DOCUMENTS

| | | | |
|---|---|---|---|
| 5,370,685 | A | 12/1994 | Stevens |
| 5,545,214 | A | 8/1996 | Stevens |
| 5,733,323 | A | 3/1998 | Buck et al. |
| 5,814,097 | A | 9/1998 | Sterman et al. |
| 7,018,406 | B2 | 3/2006 | Seguin et al. |
| 7,892,281 | B2 | 2/2011 | Seguin et al. |
| 8,652,202 | B2 | 2/2014 | Alon et al. |
| 8,747,459 | B2 | 6/2014 | Nguyen et al. |
| 9,345,877 | B2 * | 5/2016 | Pignato ................ A61N 1/3752 |
| 9,566,418 | B2 * | 2/2017 | Von Malmborg ... A61B 5/0215 |
| 2002/0198583 | A1 | 12/2002 | Rock et al. |
| 2004/0210259 | A1 | 10/2004 | Rock et al. |
| 2006/0241704 | A1 | 10/2006 | Shuros et al. |
| 2008/0008688 | A1 * | 1/2008 | Stokes ................ C07K 14/705 424/93.21 |
| 2009/0270941 | A1 | 10/2009 | Mokelke et al. |
| 2009/0318943 | A1 | 12/2009 | Eidenschink et al. |
| 2009/0318993 | A1 * | 12/2009 | Eidenschink ........ A61N 1/3758 607/10 |
| 2010/0010551 | A1 | 1/2010 | Shuros et al. |
| 2011/0230928 | A1 | 9/2011 | Shuros et al. |
| 2011/0251683 | A1 | 10/2011 | Tabor |
| 2012/0130220 | A1 | 3/2012 | Maskara et al. |
| 2013/0096555 | A1 | 4/2013 | Krom et al. |
| 2013/0172924 | A1 | 7/2013 | Mokelke et al. |
| 2013/0178908 | A1 | 7/2013 | Huber |
| 2013/0268014 | A1 | 10/2013 | Shuros et al. |
| 2014/0074227 | A1 | 3/2014 | Tabor |
| 2015/0032027 | A1 * | 1/2015 | Lupton ................ A61M 25/09 600/585 |
| 2016/0082248 | A1 | 3/2016 | Shuros et al. |
| 2017/0266434 | A1 * | 9/2017 | Daniels ................ A61M 25/09 |
| 2017/0266439 | A1 | 9/2017 | Shuros et al. |

FOREIGN PATENT DOCUMENTS

| | | |
|---|---|---|
| WO | 97/28807 A1 | 8/1997 |
| WO | 2016/162315 A1 | 10/2016 |

OTHER PUBLICATIONS

Written Opinion for Corresponding International Application No. PCT/EP2017/075362 dated Dec. 12, 2017.
"Registry of Transcatheter Aortic-Valve Implantation in High-Risk Patients", Gilard et al; the New England Journal of Medicine: p. 1705-1715 (2012); cited in the specification.
"Left Ventricular Guidewire Pacing to Simplify Aortic Balloon Valvuloplasty", Susanne Navarini et al; Catheterization and Cardiovascular Interventions 73: p. 426-427 (2009); cited in the specification.
"A novel Approach for Transcoronary Pacing in a Porcine Model", Roland Prodzinsky et al; Journal of Invasive Cardiology 24(9): p. 451-455 (2012); cited in the specification.
"Optimizing of Transcoronary Pacing in a Porcine Model", Konstantin M. Heinroth, et al, Journal of Invasive Cardiology 21, p. 634-638 (2009); cited in the specification.

* cited by examiner

ASSEMBLY FOR REPLACING A HEART VALVE OR A CORONARY ANGIOPLASTY ASSEMBLY

TECHNICAL FIELD

The present invention relates to an assembly for replacing a heart valve by the percutaneous route or to a coronary angioplasty assembly, comprising a valve delivery catheter and, where applicable, an introduction device, commonly called "introducer".

The present invention more specifically relates to the improvement of replacement assistance through cardiac stunning by means of a cardiac stimulator.

Even though it is described with reference to the replacement of an aortic valve, the assembly according to the invention can be used as a coronary angioplasty assembly that may or may not require the fitting of a prosthesis, which is commonly called "stent", in particular in an emergency situation or even in complex intervention procedures.

Similarly, even though it is described with reference to the replacement of an aortic valve, the assembly according to the invention also equally can be applicable for the replacement of another valve of the heart, such as the tricuspid valve or the mitral valve.

In general, the introducer and/or the delivery catheter of the assembly according to the invention can be inserted inside a patient by the percutaneous route and, more specifically, by the transfemoral route, by the transaortic route, by the carotidian route or by the subclavian route.

PRIOR ART

A widely known heart disease is that which is associated with the narrowing of the tricuspid valve or of the aortic heart valve through calcification, with said aortic heart valve being the valve that separates a heart cavity, namely the left ventricle of the aorta and which, in the open position, allows blood to flow from the heart to the rest of the organism of a human being.

Tight or very tight narrowing prevents the aortic valve from opening normally and therefore generates the disease that is also called calcified aortic stenosis.

The treatment for this disease involves replacing the defective aortic heart valve.

The replacement of a defective aortic heart valve is most often carried out by opening the thorax, subjecting the patient to extracorporeal circulation, implementing temporary cardiac arrest, and opening the heart, in order to remove and replace the native valve with an artificial valve or prosthesis.

The major disadvantages of these successive steps of the operation are that they involve relatively long hospitalization of the patient, they are complex and expensive and can only be reserved for some of the affected patients, since in many cases the doctor(s) and/or surgeon(s) consider that the surgical intervention referred to as "open-heart surgery" cannot be undertaken since it is too risky given the general state of health of the patient, particularly due to the necessary stopping of the heart and the related extracorporeal circulation.

In order to overcome this disadvantage, it has been contemplated for a heart valve to be replaced by a route that is minimally invasive but is still subject to extracorporeal circulation. In this case, international patent applications WO 93/01768 and WO 97/28807, as well as American patents U.S. Pat. Nos. 5,814,097, 5,370,685 or 5,545,214 can be cited that disclose known minimally invasive techniques, as well as instruments for implementing these techniques.

However, the existing techniques have been considered to be not entirely satisfactory and as having potential for improvement.

In particular, the major disadvantages of these techniques are as follows:

requiring, in any event, that the patient is subject to extracorporeal circulation; they are difficult to put into practice;

not allowing precise control of the diameter at which the native valve is cut, with a view to the subsequent calibration of the prosthetic valve;

leading to risks of spreading fragments of native valve, which are often calcified, into the organism, which can result in an embolism;

involving risks of perforating the aortic or cardiac wall;

involving risks of acute blood reflux during the ablation of the native valve.

In order to address the shortfalls of these techniques, one approach has been to fit artificial aortic valves, referred to as percutaneous, which is inspired from endovascular treatment techniques involving introducing a catheter inside a blood vessel, such as the aorta.

Thus, the native aortic heart valve that is defective due to calcification is replaced by an artificial valve while avoiding the normal previously described major heart surgery intervention.

Fitting an artificial valve currently can be performed by various percutaneous routes: by the transfemoral route, i.e. by introduction from the femoral artery to the heart, or by the transapical route or by the transaortic route, or by the carotidian route or even by the subclavian route, i.e. any route requiring neither an open-heart operation through opening of the thorax nor extracorporeal circulation.

In itself the operation involves depositing an artificial valve (prosthesis), which replicates the general shape of a normal native aortic valve, at the level of the calcified (diseased) native aortic valve, with said valve being left in place and crushed by the prosthesis.

To this end, the artificial valve formed as a pericardium, which is the fine membrane surrounding the heart, of porcine or bovine origin, is previously fixed inside a radially extendable tubular metal mesh, called "stent", and is formed by assembling wires made of shape memory material, for example, made of nickel-titanium or cobalt-chromium alloy, or 316L stainless steel for coronary stents.

The valve-stent assembly is then compressed outside a tubular sheath, called delivery catheter, which can be introduced either directly into an artery or inside an introducer allowing access to the artery whilst maintaining hemostasis.

An interventional physician then slides the valve-stent assembly into the introducer or directly into the delivery catheter until said assembly reaches the diseased aortic valve. The valve-stent assembly is subsequently deposited in the vicinity of the diseased valve by expanding a balloon before fitment.

Valve delivery catheters also exist that comprise a valve-stent assembly without a balloon, in which the valve is self-expandable, which allows the valve to be deposited, which expands radially through simple withdrawal of the sheath surrounding it and therefore without having to previously expand a balloon.

For further information, please refer to American patents U.S. Pat. Nos. 7,018,406, 7,892,281, 8,652,202 and 8,747,459.

During actual fitting, the heart needs to be temporarily stopped for a short period of time through rapid ventricular stimulation in order to minimize the transvalvular, i.e. between valvules, flow rate and to prevent, and at the very least to reduce, potential embolization.

This temporary stopping of the heart, also commonly called "cardiac stunning", thus involves causing the heart to voluntarily beat at 150 to 200 beats per minute so that there is no longer effective contraction, which causes a drop in pressures and stimulates tachycardia or ventricular fibrillation and therefore a stabilization of the heart.

This stabilization of the heart allows the balloon to be stabilized and therefore allows an increase in the precision of the fitting of the artificial valve in a matter of seconds.

Bipolar stimulation catheters exist with two electrodes, called drive or electro-systolic stimulation probes, for temporary endocardiac stimulation of the right ventricle.

These electro-systolic stimulation probes have a certain number of disadvantages that are described hereafter.

Firstly, such a probe forms a central intravenous infusion with an additional risk of vascular complications for the targeted patient population, which is weak. The French register denoted "France 2" that lists aortic valve replacement interventions, commonly denoted as TAVI (Transcatheter Aortic Valve Implantation), has indicated a resulting high risk level of vascular complications equal to 4.7%. This result is listed on page 1709 of publication [1].

Secondly, this probe is relatively rigid, and for this reason fitting it into the right ventricle, which is fragile and the wall of which is thinner than that of the left ventricle, results in a consequential risk of the phenomenon that is well known to interventional physicians as "tamponade", which means a significant circulatory deficiency that can lead to the death of the patient.

It is also to be noted that this risk also exists during the operation, i.e. when fitting the electro-systolic probe, but also post-operation as a result of the mobilization of patients in their beds and therefore of the probe that is still present, which can then pierce through the wall of the right ventricle.

Furthermore, there is a risk of moving the electro-systolic stimulation probe during the crucial moment of fitting the valve. Indeed, a stimulation probe is not fastened to a wall of the heart and therefore can move and thus result in a loss of capture of the electrical stimulation signal.

The heart is then no longer stimulated and therefore has significant movements that disrupt the placement of the valve or of the balloon.

Another risk associated with the use of such probes is the risk of infection at the puncture site. The France 2 register has indicated a rate of less than 1%: see publication [1].

Finally, an interventional physician considers that the additional operating time associated with fitting a temporary stimulation probe is significant, which operation is not always simple to perform.

Publication [2] emphasizes the advantages of performing this ventricular stimulation on the left ventricle and not on the right ventricle and of performing this operation not by means of a specific stimulation catheter by the transvenous route, but by implementing an external cardiac stimulator with the guide wire used for interventions of this type.

Thus, the recommended practice that is disclosed in this publication [2] involves using the guide wire, which supports the expansion balloon of the stent and is introduced into the left ventricle, as a part connected to the cathode of a cardiac stimulator and a cutaneous electrode or needle inserted in the subcutaneous tissue, as a support for the anode of the cardiac stimulator.

Publications [3] and [4] confirm, in the event of a coronary angioplasty intervention on a porcine population, the effectiveness of a temporary cardiac stimulation with a lower electrical stimulation voltage, by implementing the guide wire supporting the expansion balloon of the stent, as a part connected to the cathode of a cardiac stimulator and of a cutaneous electrode or needle inserted in the subcutaneous tissue, as a support for the anode of the cardiac stimulator.

Thus, the advantages of these recommended practices involve avoiding having to insert an additional dedicated catheter, avoiding additional access to the heart, reducing the time and the cost of the operation, but also reducing the level of complications associated with the insertion of the dedicated catheter, all the while allowing equally effective stimulation as by means of a stimulation by the transvenous route.

Furthermore, compared to the probes for electro-systolic stimulation of the right ventricle that lead to the risk of tamponade as explained above, the guide wire that is used for this technique is very stable and comes into permanent abutment against the wall of the relatively thick left ventricle, since it acts as a rail for advancing the stent-balloon-valve assembly through the valve.

Nevertheless, this technique still requires the fitting of an additional subcutaneous electrode or needle that must be precise, and the fitting and retention of connection clips, of the crocodile type, on two remote supports.

The inventor of the present invention has filed patent application WO2016/162315, which discloses and claims the integration of an electrode of a cardiac stimulator directly into the introduction sheath (introducer or delivery catheter) in the artery of a patient. The proposed invention makes it easier and quicker to fit and handle cardiac stimulator electrodes for the surgeon(s) responsible for the operation.

The disadvantage of this application is that it requires the production of specific introducers or delivery catheters.

However, it would be worthwhile being able to have one or more solutions that can be adapted to the existing introducers or catheters, i.e. those without an electrode integrated therein.

The aim of the invention is to at least partly address this requirement.

DISCLOSURE OF THE INVENTION

To this end, the aim of the invention, according to a first alternative, is an assembly for replacing a heart valve by the percutaneous route, comprising:
  a device forming an introducer comprising at least one tubular introduction sheath, intended to be introduced into an artery of a human body and to allow through a surgical intervention device, such as a delivery catheter;
  a sleeve adapted to be fitted around the introduction sheath, the sleeve being made of electrically conductive material on at least one part of the outer periphery thereof so that, when the sheath is introduced into the artery of a human body with the sleeve fitted around the sheath, the conductive periphery of the sleeve is in contact with the subcutaneous tissue of the body or with the artery, the sleeve further comprising an electrical connection to an electrode of a cardiac stimulator outside the body;
  at least one guide wire intended to be introduced into the tubular sheath of the introducer in order to advance an artificial valve intended to replace the heart valve, the guide wire comprising a metal part also acting as a connection to the other electrode of the external cardiac stimulator.

According to a second alternative, the aim of the invention is an assembly for replacing a heart valve by the percutaneous route, comprising:
- a device forming a valve delivery catheter comprising at least one tubular introduction sheath, intended to be introduced into an artery of a human body;
- a sleeve adapted to be fitted around the introduction sheath, the sleeve being made of electrically conductive material on at least one part of the outer periphery thereof so that, when the sheath is introduced into the artery of a human body with the sleeve fitted around the sheath, the conductive periphery of the sleeve is in contact with the subcutaneous tissue of the body or with the artery, the sleeve further comprising an electrical connection to an electrode of a cardiac stimulator outside the body;
- at least one guide wire intended to be introduced into the tubular sheath of the delivery catheter in order to advance an artificial valve intended to replace the heart valve, the guide wire comprising at least one metal part also acting as a connection to the other electrode of the external cardiac stimulator.

According to one embodiment, the electrode of the cardiac stimulator connected to the electrically conductive sleeve fitted around the introduction sheath of the introducer or of the delivery catheter is the anode, whereas that which is connected to the metal part of the guide wire is the cathode.

A further aim of the invention is an electrically conductive sleeve intended for an assembly as previously described.

The sleeve can be formed by a one-piece part made of conductive material, such as carbon.

It also can be formed by a sheath comprising an electrically conductive coating, such as a carbon coating, on the outer periphery thereof.

According to one advantageous embodiment, the sleeve can be resilient so as to be able to be fitted onto sheaths for introducers or delivery catheters with different diameters, typically with outer diameters between 1.67 and 8 mm (between 5 and 24 French gauge). Typically, the outer diameters can be 4 mm, 4.67 mm, 5.33 mm or even 6 mm for sheaths intended for heart valve replacement assemblies.

According to a third alternative, the invention relates to an assembly for replacing a heart valve by the percutaneous route, comprising:
- a device forming an introducer comprising at least one tubular introduction sheath, intended to be introduced into an artery of a human body and to allow through a surgical intervention device, such as a delivery catheter;
- a transcutaneous electrode comprising an adhesive part intended to be adhered to the skin of the human body into which the sheath is introduced, and a part made of electrically conductive material so that, when the adhesive part is adhered to the skin, the conductive part can deliver a current transcutaneously, the conductive part further comprising an electrical connection to an electrode of a cardiac stimulator outside the body;
- at least one guide wire intended to be introduced into the tubular sheath of the introducer in order to advance an artificial valve intended to replace the heart valve, the guide wire comprising a metal part also acting as a connection to the other electrode of the external cardiac stimulator.

According to a fourth alternative, the aim of the invention is an assembly for replacing a heart valve by the percutaneous route, comprising:
- a device forming a valve delivery catheter comprising at least one tubular introduction sheath, intended to be introduced into an artery of a human body;
- a transcutaneous electrode comprising an adhesive part intended to be adhered to the skin of the human body into which the sheath is introduced, and a part made of electrically conductive material so that, when the adhesive part is adhered to the skin, the conductive part can deliver a current transcutaneously, the conductive part further comprising an electrical connection to an electrode of a cardiac stimulator outside the body;
- at least one guide wire intended to be introduced into the tubular sheath of the delivery catheter in order to advance an artificial valve intended to replace the heart valve, the guide wire comprising at least one metal part also acting as a connection to the other electrode of the external cardiac stimulator.

According to one embodiment, the electrode of the cardiac stimulator connected to the transcutaneous electrode is the anode, whereas that which is connected to the metal part of the guide wire is the cathode.

A further aim of the invention is a transcutaneous electrode, intended for an assembly as previously described.

According to a fifth alternative, a further aim of the invention is an assembly for replacing a heart valve by the percutaneous route, comprising:
- a device forming an introducer comprising at least one tubular introduction sheath, intended to be introduced into an artery of a human body and to allow through a surgical intervention device, such as a delivery catheter;
- at least one guide wire, called bipolar guide wire, intended to be introduced into the tubular sheath of the introducer in order to advance an artificial valve intended to replace the heart valve, the guide wire comprising a metal core coated with an electrically isolating sheath on a central portion between the proximal end and the distal end of the guide wire, the metal core being non-electrically isolated on the remainder of the length of the guide wire, the electrically isolating sheath integrating an electrically conductive element, for which a distal portion is apparent on at least one part of the outer periphery of the isolating sheath so as to be in contact with the subcutaneous tissue of the body or with the artery and for which a proximal portion is apparent on at least one part of the outer periphery of the isolating sheath so as to be accessible from outside the body when the guide wire is introduced into the introduction sheath, with the proximal portion acting as a connection to an electrode of a cardiac stimulator outside the body, whereas the metal core of the bipolar guide wire acts as a connection to the other electrode of the external cardiac stimulator.

According to a sixth alternative, the aim of the invention is an assembly for replacing a heart valve by the percutaneous route, comprising:
- a device forming a valve delivery catheter comprising at least one tubular introduction sheath, intended to be introduced into an artery of a human body;
- at least one guide wire, called bipolar guide wire, intended to be introduced into the tubular introduction sheath in order to advance an artificial valve intended to replace the heart valve, the guide wire comprising a metal core coated with an electrically isolating sheath on a central portion between the proximal end and the distal end of the guide wire, the metal core being non-electrically isolated on the remainder of the length of the guide wire, the electrically isolating sheath integrating an electrically conductive element, for which a distal portion is apparent on at least one part of the outer periphery of the isolating sheath so as to be in contact with the subcutaneous tissue of the body or with the artery and for which a proximal portion is apparent on at least one part of the outer periphery of the isolating sheath so as to be accessible from outside the body when the guide wire is introduced into the introduction sheath, with the proximal portion acting as a connection to an electrode of a cardiac stimulator outside the body, whereas the metal core of the bipolar guide wire acts as a connection to the other electrode of the external cardiac stimulator.

According to one embodiment, the electrode of the cardiac stimulator connected to the electrically conductive element integrated in the sheath of the guide wire is the anode, whereas that which is connected to the metal core of the guide wire is the cathode.

According to an advantageous variation of the invention, the metal conductive element is a metal layer embedded in the isolating sheath, except for its apparent distal and proximal portions.

According to one embodiment, the non-electrically isolated distal end of the metal core of the guide wire intended to come into contact with the wall of the left ventricle of the heart of a patient is a portion that is more flexible than the remainder of the guide wire. Preferably, the more flexible portion is adapted to wrap around itself when it comes into contact with the wall of the left ventricle of the heart of a patient.

The distal portion of the conductive element can be connected to an electrical connection, which is intended to be connected to an electrode of the cardiac stimulator outside the body.

A further aim of the invention is a bipolar guide wire intended for an assembly as previously described. Such a bipolar guide wire comprises a metal core coated with an electrically isolating sheath on a central portion between the proximal end and the distal end of the guide wire, the metal core being non-electrically isolated on the remainder of the length of the guide wire, the electrically isolating sheath integrating an electrically conductive element, for which a distal portion is apparent on at least one part of the outer periphery of the isolating sheath and for which a proximal portion is also apparent on at least one part of the outer periphery of the isolating sheath.

While seeking an alternative to the solution disclosed in the aforementioned application WO2016/162315, the inventor searched among the already existing solutions for cardiac stimulation.

They then tested a known stimulation electrode intended for temporary transcutaneous cardiac stimulation. This technique is proposed in the treatment of symptomatic bradycardia in an emergency situation or to prevent a tachyarrhythmia of a heart.

However, no one had considered testing such an electrode with a view to achieving cardiac stunning.

Surprisingly, by connecting the cathode of an external cardiac stimulator to the guide wire of an artificial valve and the anode to a transcutaneous electrode in contact with the skin of the patient, the inventor obtained effective cardiac stunning.

The inventor also considered integrating the metal support of an electrode of the cardiac stimulator into a part fitted around the introduction sheath that is introduced into the artery of a patient. The sleeve according to the invention therefore is in direct contact with the artery of the patient.

Finally, the inventor considered integrating the metal support of an electrode of the cardiac stimulator, not directly into the introduction sheath in the artery of a patient as in the aforementioned application, but into a guide wire.

The bipolar guide wire according to the invention on its own acts as a support for the two electrical connections respectively connected to the anode and to the cathode of an external cardiac stimulator. Thus, the metal core acts as a support for one of the electrical connections, whereas the proximal portion of the conductive element, which is isolated from the metal core, acts as a support for the other one of the electrical connections.

Cardiac stunning thus can be performed by bipolar electrical stimulation, the advantage of which is that it requires a very low electrical stimulation threshold.

The introduction sheath can be that of an introducer or directly that of a delivery catheter, which is smaller compared to an introducer. A valve delivery catheter does not de facto require an introducer since it can be introduced directly into the artery of a patient.

By virtue of the various alternatives of the invention, a needle no longer needs to be inserted in the subcutaneous tissues or a cutaneous electrode in order to act as a support for the electrode, typically the anode of a cardiac stimulator.

Furthermore, the use and fitting of an electro-systolic probe as in the prior art, commonly called temporary probe, is no longer required.

Furthermore, by virtue of the invention, the stimulation intensity required for cardiac stunning is lower than in the solutions of the prior art, due to a lower impedance of the vascular system relative to the subcutaneous tissue. Typically, the intensity of the current delivered with a view to cardiac stunning can range from 10 to 20 mA and the delivered voltage can range from 0.5 to 10 Volt.

The surgeon(s) responsible for the operation thus can easily connect the electrode, typically the anode of the cardiac stimulator, to the conductive sleeve fitted around the introducer or the delivery catheter or even the transcutaneous electrode or even the bipolar guide wire, then connect the other electrode as normal, typically the cathode to the guide wire of the valve-stent-balloon or self-expanding-valve-stent assembly.

Thus, the step of preparing for heart stoppage is easier and quicker to implement.

Furthermore, the inventor considers that a sleeve or a transcutaneous electrode or a bipolar guide wire according to the invention can reduce the risks of complications associated with the electro-systolic stimulation probes of the prior art that are placed in the right ventricle.

The introducer or the delivery catheter can be introduced by the transapical route or by the transfemoral route as normal, which route is preferred due to its less invasive nature for weaker patients.

The introducer or the delivery catheter can integrate a peripheral perfusion system, commonly called "flush" system, which can be fitted to clean any blood clots out of the inside of the introducer or the catheter that are likely to be present therein.

Thus, advantageously, for an assembly for replacing an aortic heart valve, the introducer can be a known introducer, for example, that with the *"Edwards eSheath introducer sheath set"* trade name, marketed by Edwards Lifesciences.

The artificial valve can be introduced and positioned in the artery by means of a conventional catheter valve, which is introduced into the introducer. The artificial valve then assumes a folded position and does not obstruct the introduction and sliding of the catheter valve into the introducer and then into the artery, or into the delivery catheter according to the invention, and then into the artery.

Subsequently, in the deployed position, the artificial valve comes into abutment against the outer wall of the native heart valve in place of said valve by crushing said valve.

A conventional catheter valve thus allows the artificial valve to be introduced and positioned at the suitable location, using the same operating movement as that which allows the native valve to be opened and crushed. Following the opening and crushing of said native valve, the catheter valve is caused to axially slide in the distal direction in order to convey the artificial valve to the appropriate level in the opening of the native valve.

The surgeon(s) operating on the patient applies, during the opening and crushing of the native valve, then afterwards, a cardiac stimulation by means of the external cardiac stimulator, with the electric current circulating between the cathode and the anode of the stimulator, the cathode being connected to the guide wire of the artificial valve and the anode being connected to the conductive sleeve according to the invention, which is fitted around the external tubular sheath of the introducer or of the delivery catheter and is in contact with the subcutaneous tissue of the patient or with the inner wall of the artery.

The artificial valve is deployed at the same time as the ventricular stimulation. The catheter valve is then withdrawn.

To summarize, the advantages of an assembly according to the invention are identical to those of an assembly according to application WO2016/162315, which advantages can be listed as follows:

- simpler and quicker fitting of an electrode, typically the ventricular stimulation anode, during the defective aortic valve replacement operation;
- the elimination of the need to insert an additional subcutaneous needle as an electrode support, typically a cardiac stimulator anode;
- a shorter time and lower cost for the defective heart valve replacement operation;
- enhanced efficiency of the temporary stimulation with a view to achieving the desired cardiac stunning due to the lower impedance of the vascular system encountered by the electrical stimulation current, since the sleeve around an introducer or a delivery catheter is directly in contact with said system, as opposed to the needles of the prior art, which come into contact with the cutaneous tissue of a patient necessarily having higher impedance;
- enhanced efficiency of the temporary stimulation with a view to achieving the desired cardiac stunning due to the stability of the rigid guide (diameter of approximately 1.455 mm) in the left ventricle, instead of the instability of the electro-systolic probe according to the prior art that is fitted in the right ventricle;
- the possibility of performing the temporary cardiac stimulation with a lower electric current due to the lower impedance of the vascular system encountered between the two electrodes of the external stimulator;
- the elimination of the risks of complications associated with the temporary stimulation probes according to the prior art that are fitted in the right ventricle;
- the possible use of the introducer or of the delivery catheter for a plurality of different types of TAVI interventions, such as the replacement of an aortic, pulmonary, tricuspid or mitral valve. In particular, for the replacement of a degenerated tricuspid valve, only the technique of introducing a stimulation probe into the right ventricle by means of the guide rail (diameter 0.89 mm) can be contemplated, since fitting both the guide rail and an electro-systolic probe cannot be contemplated as the expansion of the balloon or of the valvular prosthesis would compress the probe, with the inherent risk of interrupting the stimulation or of blocking the stimulation probe;
- the possible use in the pediatric population during valvular or cardiac procedures on hearts with higher tachycardia, which are more mobile than in the adult population. Furthermore, this involves a population in which femoral venipuncture can be very difficult, as is the fitting of a right ventricular stimulation probe. Finally, the right ventricular walls of infants are thin and fragile, thus increasing the risk of severe complications such as tamponade. This also involves the population described in publication [2];
- the possible use in the coronary angioplasty field in emergencies and in complex procedures, in which a temporary cardiac stimulation must be performed effectively and very quickly. To this end, an introducer or a delivery catheter with a sleeve according to the invention saves the time required to fit an electrode or an additional subcutaneous needle as in the prior art, which can be a determining factor during these interventions.

The only relative limitation of the sleeve, of the transcutaneous electrode or of the bipolar guide wire according to the invention is at the start of the operation, during preparation, and involves fitting the sleeve around the introduction sheath. However, this operation is very simple and easy to implement and quite possibly can be performed by an assistant or a nurse, without them requiring special skills for this task.

A further aim of the invention is the use of the assembly with an introducer or delivery catheter with a sleeve as previously described for replacing an aortic, pulmonary, tricuspid or mitral valve.

Finally, the aim of the invention is the use of the assembly with an introducer or delivery catheter with a sleeve as previously described for a coronary angioplasty intervention, particularly in an emergency situation.

This use is particularly advantageous in three intervention situations that can be encountered in coronary angioplasty.

The first situation is the treatment of an acute heart-attack that would result in conduction problems of the extreme bradycardia type or a major auriculo-ventricular blockage. Using an introducer with a sleeve according to the invention avoids the use of an electro-systolic probe according to the prior art, which is much more invasive and requires a significant added implantation time.

The second situation relates to the treatment of calcified coronary lesions by burring that is carried out inside the coronaries in question, normally using a burring device known under the "Rotablator®" trade name. Using an introducer with a conductive sleeve according to the invention then also overcomes having to use an electro-systolic cardiac stimulation probe as in the prior art.

The third situation relates to the fitting of a stent, in certain parts of the coronaries in the vicinity of their sources (ostia), these zones are very mobile in relation to the intervention catheter, while these anatomic zones require very high precision when implanting the stent. Using an introducer with a conductive sleeve according to the invention allows the stent to be stabilized before and during its fitting.

DETAILED DESCRIPTION

Further advantages and features of the invention will become more clearly apparent upon reading the detailed description of the invention, which is provided by way of a non-limiting illustration, with reference to the following figures, in which.

Throughout the following description, as well as throughout the present application, the terms "distal" and "proximal" are used with reference to the body of a patient, for which the defective native aortic valve is replaced by an artificial aortic valve. Thus, the distal end of an introducer is the end located farthest inside the patient during the replacement operation.

For the sake of simplification, the same elements in the device according to the invention and in the device according to the prior art are denoted using the same reference signs.

Please note that the various elements are not necessarily shown to scale.

Figure 1:
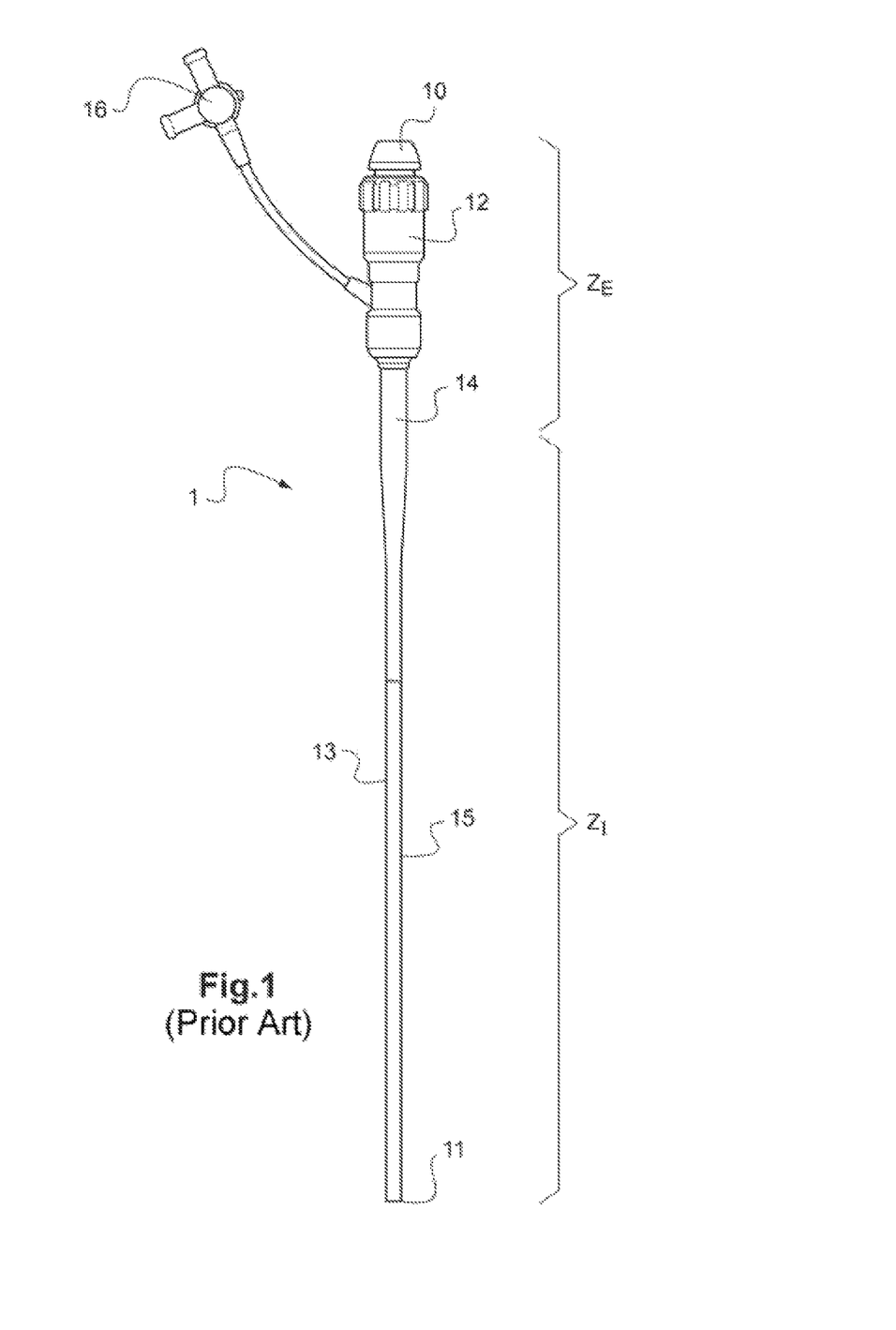
FIG. 1 is a perspective view of an introducer according to the prior art intended to be introduced into a femoral artery in the groin of a patient.

FIG. 1 shows an introducer 1 for replacing a heart valve by the transfemoral route.

This introducer 1, which is of general tubular shape, comprises, between the proximal end 10 and the distal end 11 thereof, an end piece 12 extended by at least one external tubular sheath 13 formed by two tubular portions 14, 15 from the proximal side toward the distal side, considered in relation to the introduction into a femoral artery of a patient to be operated on, i.e. from top-to-bottom in FIG. 1.

The end piece 12 generally integrates a set of sealed valves for achieving hemostasis, i.e. to ensure that blood is maintained inside the blood vessels of the patient during the operation.

The tubular sheath 13 may or may not be extendable in order to allow through a surgical intervention device such as a catheter valve, as explained hereafter. The constituent material of the sheath 13 is a biocompatible material, such as silicon. It equally can be made of Teflon™ or of polyurethane. The outside of the sheath advantageously can be covered with a hydrophilic layer and the inside can be covered with a material with a low friction coefficient in order to facilitate the sliding of an intervention device.

The introducer 1 shown in FIG. 1 also comprises a tapped rinsing device 16, commonly called "flush" device, that is integrated in order to rinse the inside of the introducer 1 using a suitable rinsing liquid.

All the elements of the introducer 1 present in the proximal or external zone $Z_E$ are intended to remain outside the body of the patient, the entirety of the distal portion 15 of the sheath 13 defining the distal zone $Z_1$ is intended to be introduced into a femoral artery of a patient.

The introducer 1 that is shown is, for example, that which is marketed under the *"Edwards eSheath introducer sheath set"* trade name, marketed by Edwards Lifesciences.

Figure 2A:
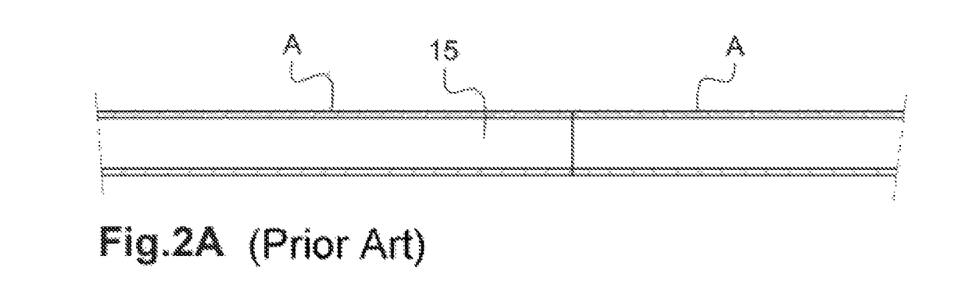
FIGS. 2A to 2C show a partial longitudinal section view of various steps of sliding a catheter valve into the introducer according to FIG. 1, in order to fit an artificial valve in place of a defective native aortic valve.
Figure 2B:
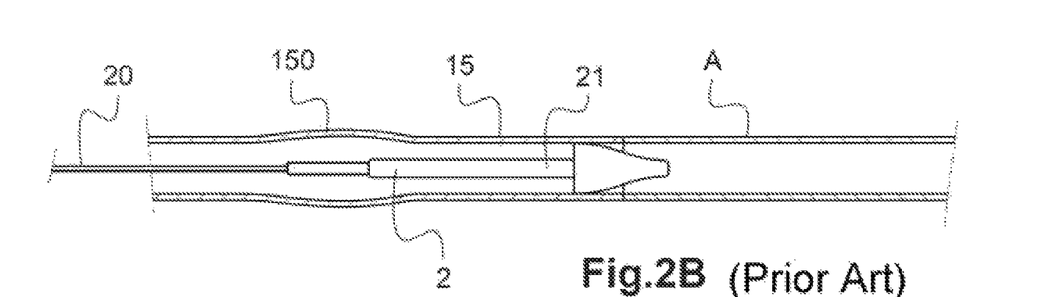
Figure 2C:
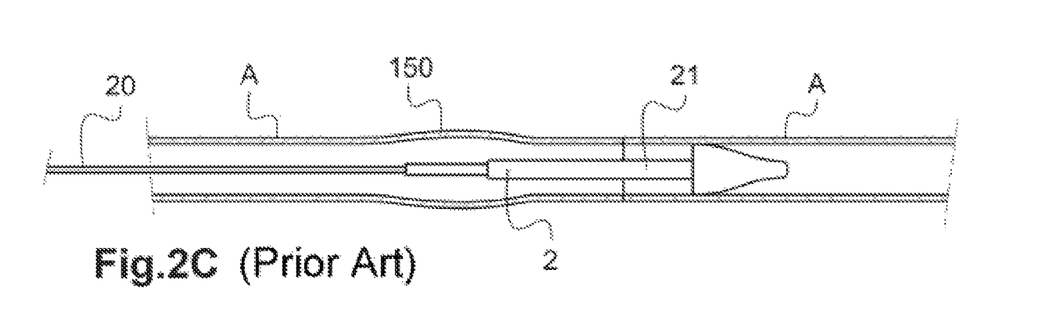

FIGS. 2A to 2C show the progression of a catheter valve 2 formed by a guide wire 20 and an assembly 21 formed by an artificial valve fixed to a radial expansion stent and a balloon that can be inflated to provide this expansion, inside the distal portion 14 of the tubular sheath of the introducer 1 already introduced into a femoral artery A.

The tip of the assembly 21 enables easy penetration into the defective native aortic valve.

These figures show that as the catheter valve 2 slides, the portion 15 of the tubular sheath temporarily radially deforms while forming a slight protuberance 150. When the tubular sheath is not extendable, it does not deform radially.

Figure 3:
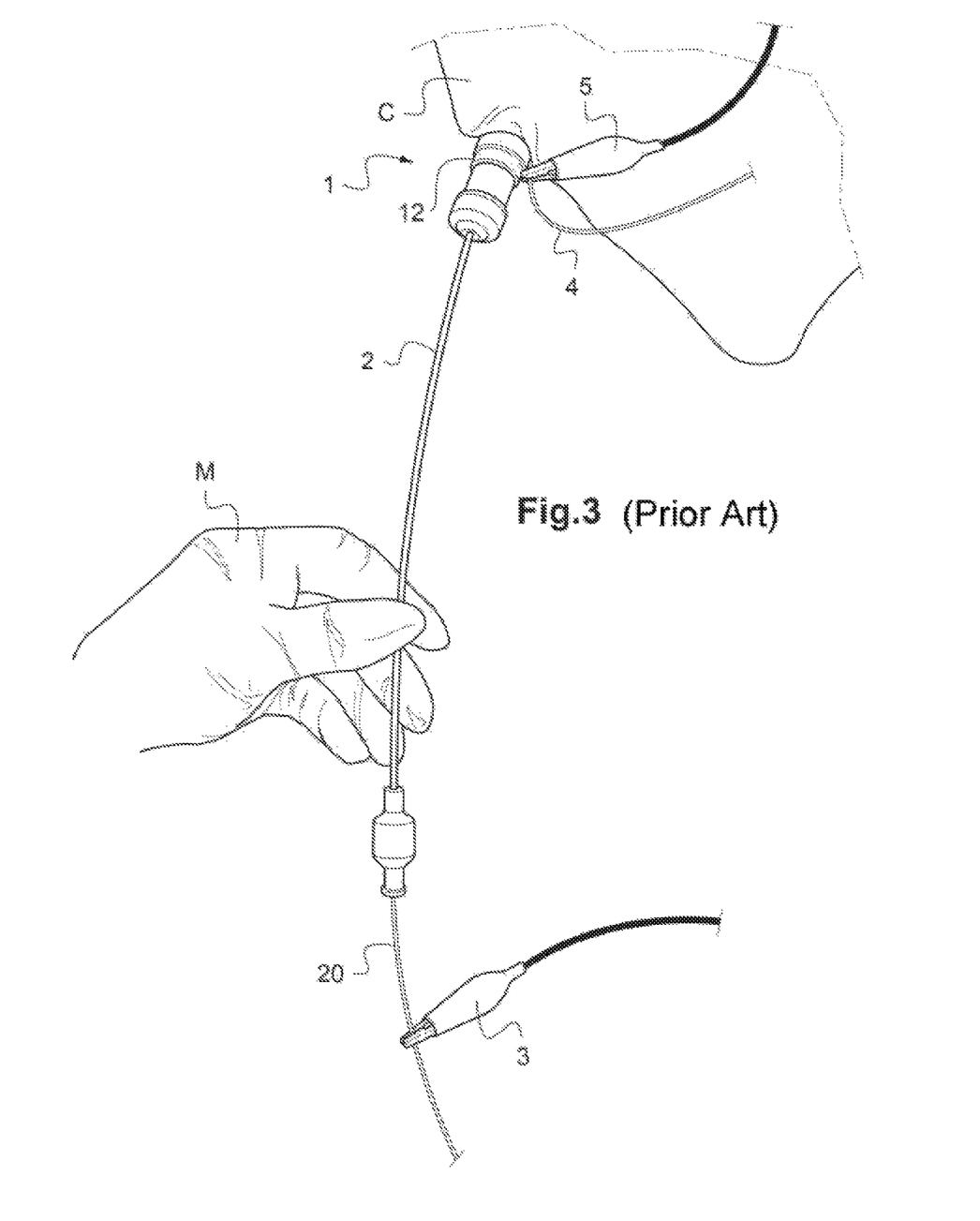
FIG. 3 shows a schematic perspective view, from outside a patient, both of the step of fitting a catheter valve and of fitting cardiac stimulation electrodes according to the prior art.

FIG. 3 shows that the hand M of a surgeon introduces the catheter valve 2 into the introducer 1 already introduced into the femoral artery of a patient, with the end piece 12 projecting outside the body C.

This introduction of the catheter valve 2 allows the assembly 21 to be brought level with the defective calcified aortic valve that needs to be replaced.

Normally, as is also shown in FIG. 3, a clip 3, known as crocodile clip, is fixed by clipping onto the guide wire 20 of the catheter valve 2. This clip 3 is connected to the cathode of a cardiac stimulator (not shown) located outside the body C.

A needle (not shown) is also inserted in the subcutaneous tissues of the body C of the patient to be operated on. A metal wire 4 is fixed on this needle.

A crocodile type clip 5 is also fixed by clipping onto the metal wire 4.

This clip 5 is connected to the anode of the cardiac stimulator outside the body.

Thus, when the artificial valve is level with the native aortic valve to be replaced, the surgeon performs, prior to the actual fitting of the artificial valve, i.e. the inflation of the balloon and therefore the expansion of the stent to which the valve is fixed, a rapid ventricular stimulation of the left ventricle.

To this end, an electrical signal is delivered between the cathode and the anode by means of the clips 3, 5, with the balloon acting as an electrical isolator between these two electrodes.

Figure 4:
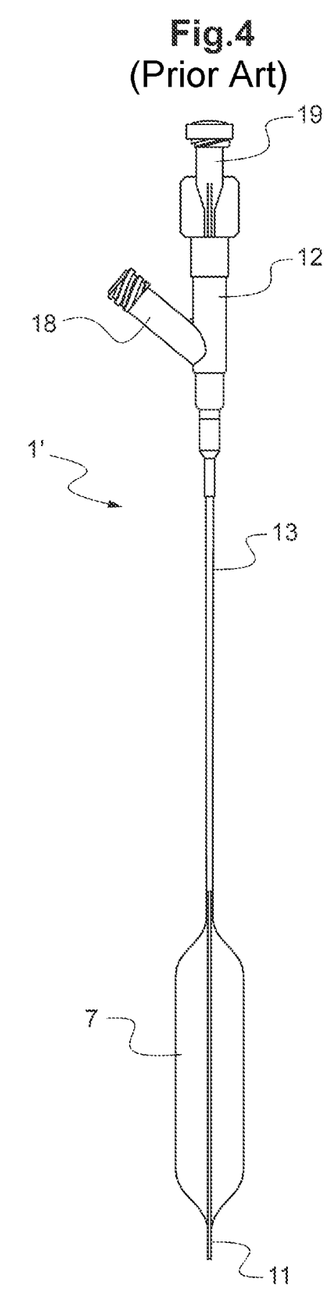
FIG. 4 is a schematic perspective view of a delivery catheter according to the prior art intended to be introduced directly into the artery of a patient without requiring an introducer.

FIG. 4 shows a delivery catheter 1' that can be introduced directly into the artery of a patient without requiring an introducer. More specifically, the catheter 1' comprises an end piece 12 extended by an introduction sheath 13. The end piece 12 comprises a connection 18 for inflating/deflating a balloon 7 at the distal end 11, which allows a prosthetic valve (not shown) to be expanded.

Faced with the numerous operations involved in replacing an aortic valve by the femoral route, as has been briefly described above, and in particular faced with the precise and delicate fitting of the additional subcutaneous needle, as well as the fitting and retention of the crocodile type connection clips on two remote supports, the inventor of the present invention has already considered integrating the metal wire 4 directly into an introducer 1 or into a delivery catheter 1'. This solution is disclosed and claimed in patent application WO2016/162315.

Even though this solution provides numerous advantages compared to the technique according to the prior art, it nevertheless has a significant disadvantage, which is the requirement to produce specific introducers or delivery catheters.

Figure 5:
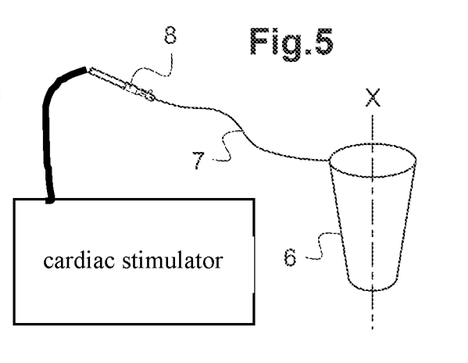
FIG. 5 is a perspective view of an electrically conductive sleeve according to the invention intended to be fitted around a device forming an introducer according to the prior art, such as that shown in FIG. 1, or around a delivery catheter according to the prior art, such as that shown in FIG. 4.

Furthermore, the inventor firstly considered integrating the function of the metal wire not in a specific introducer or delivery catheter, but for an electrically conductive sleeve 6 to be produced that is adapted to be fitted directly around an existing introducer 1 or delivery catheter 1'.

Such a sleeve 6 according to the invention is shown in FIG. 5: it is shown in the form of a tube, at least one part of the outer periphery of which is electrically conductive.

This conductive part is connected to an electrical connection 8 by means of an electrical power supply wire 7.

The sleeve 6 can be of cylindrical shape or can have a conical section. Its shape matches the external shape of the introduction sheath 13 of an introducer 1 or a catheter 1' as closely as possible.

Figure 6:
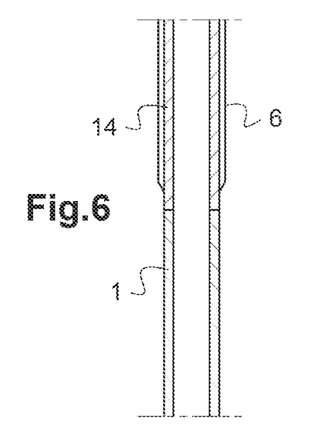
FIG. 6 is a partial longitudinal section view showing a sleeve according to FIG. 5 fitted around an introducer according to the prior art, such as that shown in FIG. 1.

As shown in FIG. 6, the thickness of this sleeve 6, which is typically approximately one millimeter or less, only adds a slight over-thickness to the sheath 13 and therefore does not hinder the progression thereof when it is introduced into an artery A.

The sleeve 6 can be produced in the form of a fully conductive one-piece part or in the form of a part coated with an electrically conductive coating. Advantageously, carbon can be selected as the electrically conductive material.

According to an advantageous variation, the sleeve 6 can be designed so that it is resilient and so that it can thus adapt to any size of existing introducer or delivery catheter.

In practice, a surgeon or interventional physician wishing to undertake an operation for replacing a heart stimulation valve with cardiac stimulation accompanying the fitting of the prosthetic valve, begins by fitting the conductive sleeve 6 around the introducer 1 or the delivery catheter 1'. As fitting the conductive sleeve is very simple and easy, it can be undertaken by an assistant or a nurse without them having to adopt any particular technique.

Fitting is complete once the sleeve 6 is fitted and arranged around the introduction sheath 13 so that it comes into contact either with a subcutaneous zone of the patient or with the wall of the aortic artery of the patient.

Once this fitting is complete, the introduction of the introducer 1 or of the delivery catheter 1' with the sleeve 6 around the sheath, can be completed normally by the surgeon.

Once the introducer 1 or the catheter 1' is positioned in the femoral artery, the electrical connection 8 can be connected directly to the anode of an external cardiac stimulator.

Normally, a clip, such as the crocodile clip 3 shown in FIG. 3, in turn can be fixed by clipping onto the guide wire of an introducer 1 or of a catheter valve 1'. This clip is connected to the cathode of the cardiac stimulator (not shown), located outside the body C.

Thus, the temporary cardiac stimulation for achieving the desired cardiac stunning can occur between the cathode electrically connected to the guide wire and the anode electrically connected to the sleeve 6 according to the invention.

Figure 7:
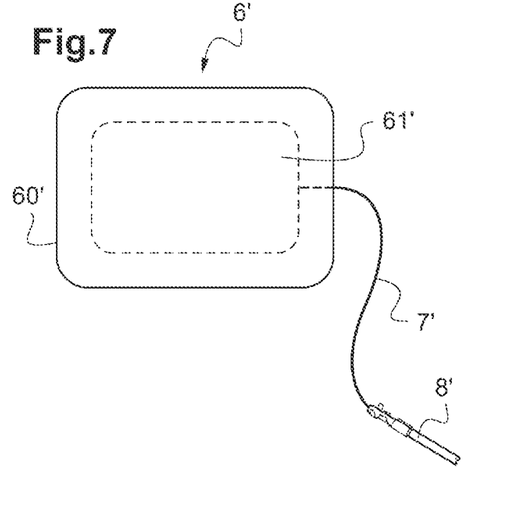
FIG. 7 is a perspective view of a transcutaneous electrode intended to be used in an assembly for replacing a heart valve by the percutaneous route, in order to achieve cardiac stunning.

The inventor has also considered integrating the function of the metal wire not in a specific introducer or delivery catheter, but for a transcutaneous electrode 6' to be used instead.

Such an electrode 6' according to the invention is shown in FIG. 7: it comprises an adhesive part 60' intended to be adhered to the skin of the human body into which the sheath is introduced, and a part 61' made of electrically conductive material adapted to deliver a current transcutaneously.

The part 61' made of conductive material further comprises an electrical connection, including an electrical power supply wire 7' rigidly connected to a connector 8 in order to complete the connection with an electrode of an external cardiac stimulator.

In practice, a surgeon or interventional physician wishing to undertake an operation for replacing a heart stimulation valve with cardiac stimulation accompanying the fitting of the prosthetic valve, begins by adhering the transcutaneous electrode 6 to the skin of the patient. This electrode can be fitted, for example, in a zone facing the heart. As fitting is very simple and easy, it can be undertaken by an assistant or a nurse without them having to adopt any particular technique.

Once this fitting is complete, the surgeon can introduce the introducer 1 or the delivery catheter 1' as normal.

Once the introducer 1 or the catheter 1' is positioned in the femoral artery, the electrical connection 8 can be connected directly to the anode of an external cardiac stimulator.

Figure 8:
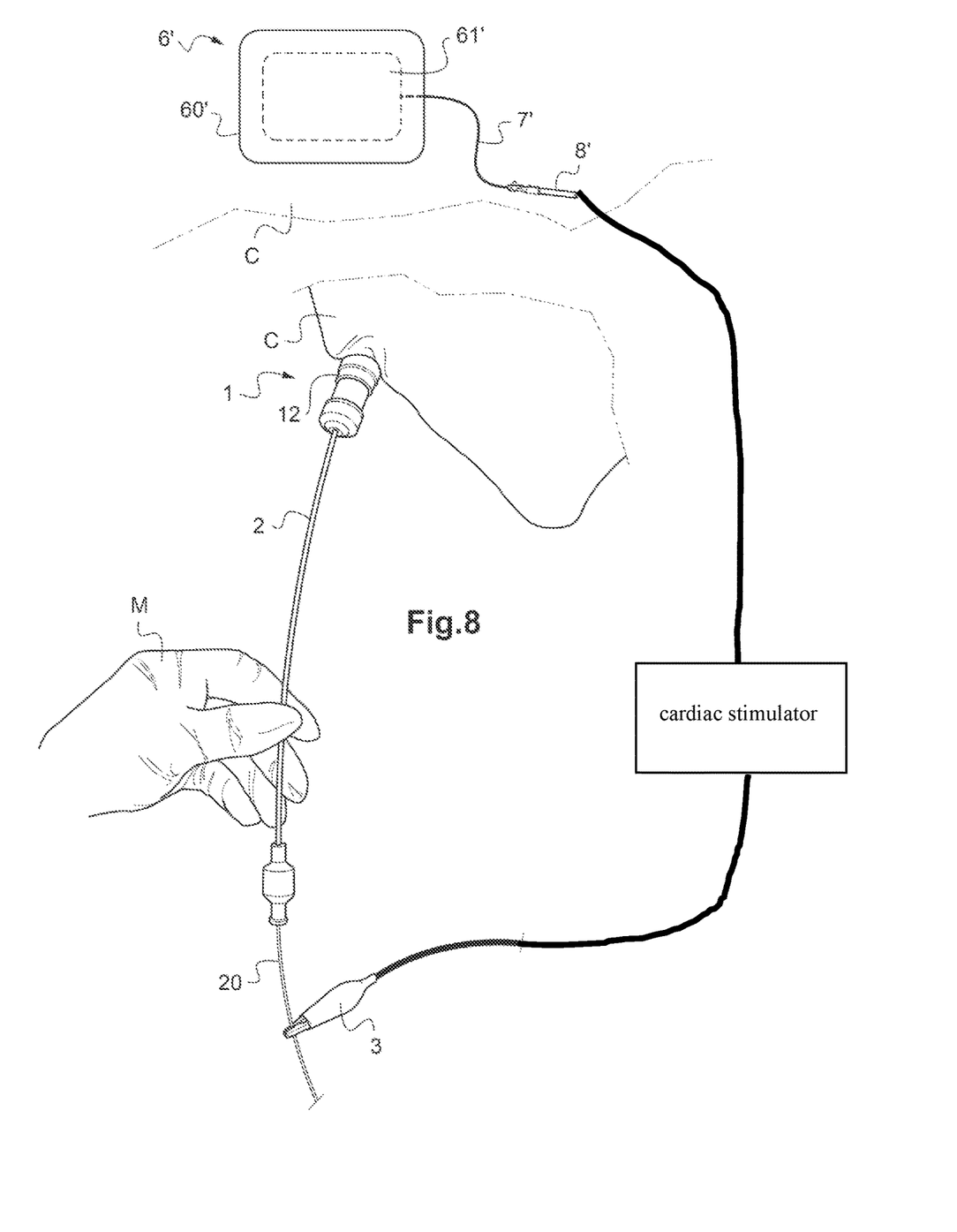
FIG. 8 shows a schematic perspective view, from outside a patient, both of the step of fitting a catheter valve and of fitting cardiac stimulation electrodes according to the invention.

Normally, a clip, such as a crocodile clip 3, in turn can be fixed by clipping onto the guide wire of an introducer 1 or of a catheter valve 1'. This clip is connected to the cathode of the cardiac stimulator (not shown), located outside the body C. Such a configuration is shown in FIG. 8.

Thus, the temporary cardiac stimulation for achieving the desired cardiac stunning can occur between the cathode electrically connected to the guide wire and the anode electrically connected to the transcutaneous electrode 6' according to the invention.

Figure 9:
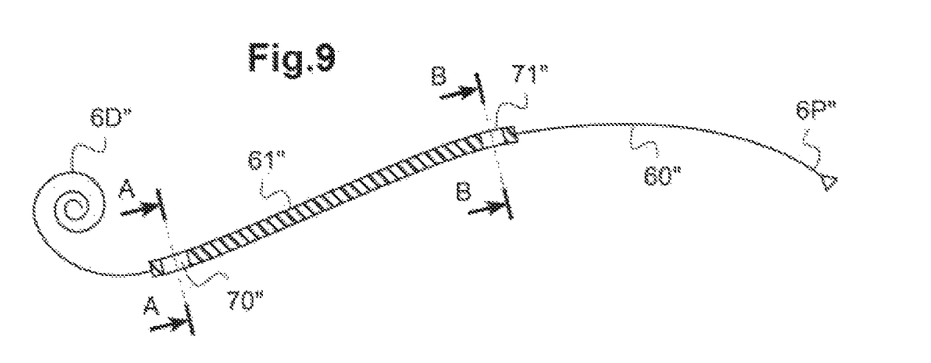
FIG. 9 is a perspective view of a bipolar guide wire according to the invention intended to be used in an assembly for replacing a heart valve by the percutaneous route, in order to achieve cardiac stunning.

Furthermore, the inventor considered integrating the function of the metal wire not in a specific introducer or delivery catheter, but in a bipolar guide wire 6" with electrical isolation on its central portion, with the guide wire still being intended to be introduced into the tubular sheath 13 of the introducer.

Figures 9A, 9B:
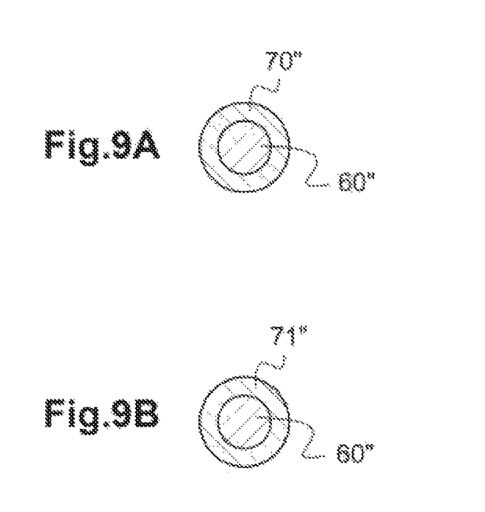
FIGS. 9A and 9B are transverse section views along A-A and along B-B, produced at the level of the distal and proximal portion, respectively, of the electrically conductive element embedded in the isolating sheath of the bipolar guide wire according to FIG. 9.
Figure 10:
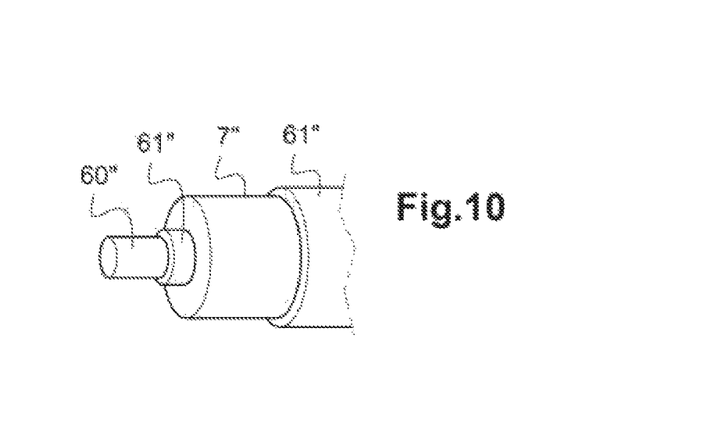
FIG. 10 shows a section view of the formation of the central portion of the bipolar guide wire according to the invention.

More specifically, as shown in FIGS. 9 to 10, the bipolar guide wire 6" firstly comprises a metal core 60" coated with an electrically isolating sheath 61" on a central portion between the proximal end 6P" and the distal end 6D" of the guide wire.

The distal end 6D" of the metal core is intended to come into contact with the wall of the left ventricle of the heart of a patient.

In the embodiment shown, this distal end 6D" is a more flexible portion than the remainder of the guide wire, with its flexibility allowing it to wrap around itself when it comes into contact with the wall of the left ventricle of the heart of a patient. This thus ensures contact that is both secure and non-impacting, i.e. that does not risk perforating the wall of the ventricle, contrary to the electro-systolic stimulation probes according to the prior art, with which contact is quasi-punctual contact with the wall, which generates a risk of tamponade.

The metal core 60" is non-electrically isolated on the remainder of the length of the guide wire.

A metal layer 7" is embedded inside the electrically isolating sheath 61", with the exception of the distal 70" and proximal 71" portions thereof.

Thus, the distal portion 70" is apparent over the entire outer periphery of the isolating sheath 71" in order to be in contact with the subcutaneous tissue of the body or with the artery. The proximal portion 71" is apparent over the entire outer periphery of the isolating sheath in order to be accessible from outside the body C when the guide wire is introduced into the introduction sheath 13.

By means of this formation of the bipolar guide wire 6", the proximal portion 71" of the integrated conductive element 7" acts as a connection to an electrode of a cardiac stimulator outside the body, whereas the metal core 60" of the bipolar guide wire acts as a connection to the other electrode of the external cardiac stimulator.

In practice, a surgeon or interventional physician wishing to undertake an operation for replacing a heart stimulation valve with cardiac stimulation accompanying the fitting of the prosthetic valve, begins by introducing the introducer 1 or the delivery catheter 1', which can be undertaken by the surgeon as normal.

The bipolar guide wire 6" according to the invention is then introduced into the introduction sheath 13 of the introducer 1 or of the delivery catheter 1'.

Figure 11:
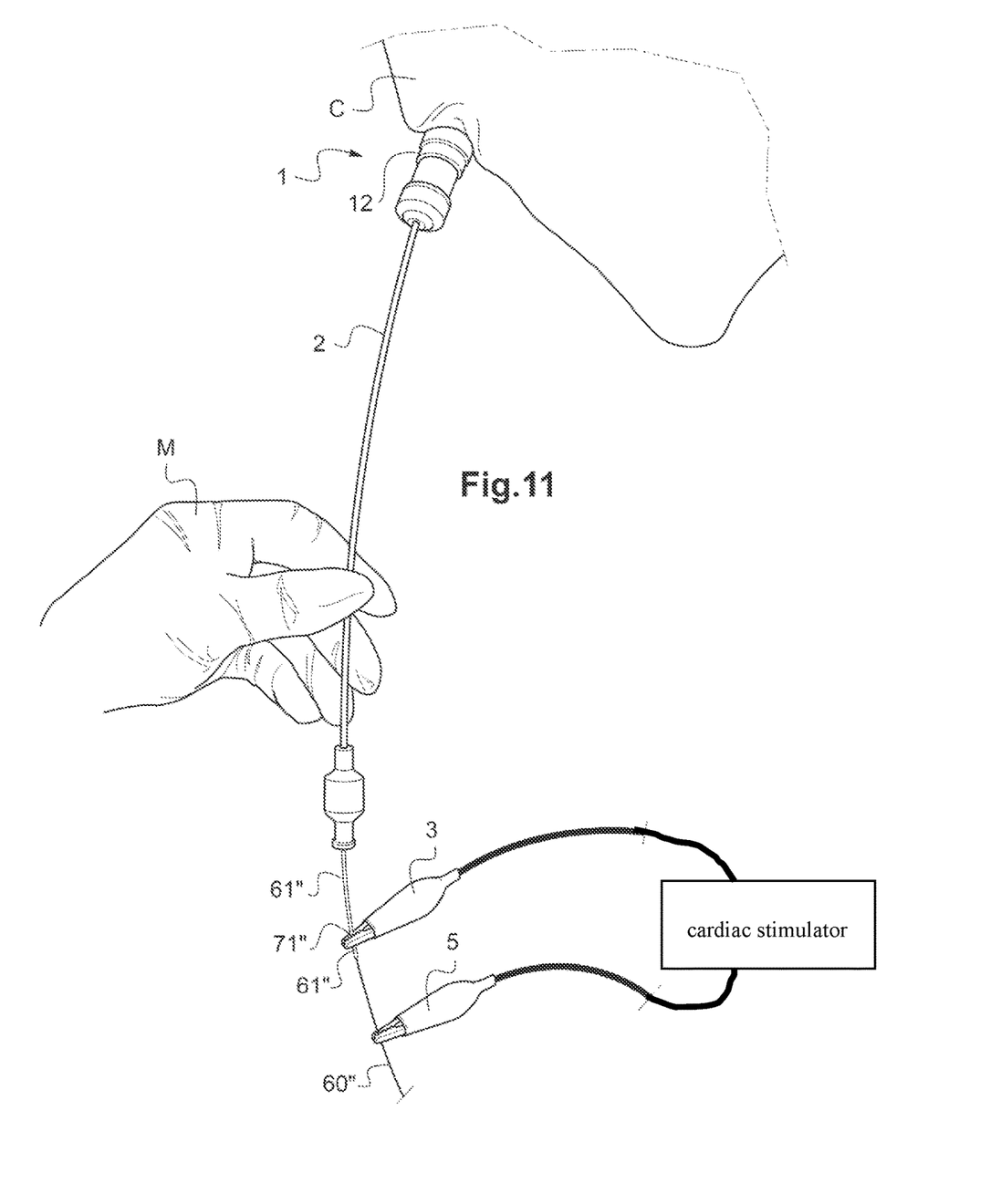
FIG. 11 shows a schematic perspective view, from outside a patient, both of the step of fitting a catheter valve and of fitting cardiac stimulation electrodes according to the invention.

Once these fittings are complete, the proximal portion 71" of the conductive element 7" can be connected directly to the anode of an external cardiac stimulator. Alternatively, as shown in FIG. 11, a clip 5, such as a crocodile clip 3, can be fixed by clipping onto the conductive proximal portion 71". This clip 3 is connected to the anode of the cardiac stimulator (not shown), located outside the body C.

Normally, a clip, such as a crocodile clip 5, in turn can be fixed by clipping onto the metal core 60" of the guide wire 6". This clip 5 is connected to the cathode of the cardiac stimulator (not shown), located outside the body C. Such a configuration is shown in FIG. 11.

Thus, the temporary cardiac stimulation for achieving the desired cardiac stunning can occur between the cathode electrically connected to the metal core 60" of the guide wire 6" according to the invention and the anode electrically connected to the distal portion 71" of the conductive element 7" of the guide wire 6".

The invention allows all the advantages to be maintained that are inherent with the invention according to application WO2016/162315 for replacing a heart valve by the percutaneous route, with the additional advantage of being able to be implemented in any existing introducer or delivery catheter, since the following can be selected:

only one conductive sleeve 6 must be fitted around said existing introducer or catheter and an electrical connection must be made with the guide wire, before they are introduced into the artery of the patient to be operated on; or only one transcutaneous electrode 6' is to be adhered to the skin of a patient with a view to cardiac stunning and a connection needs to be made with the guide wire during the replacement operation;

only two electrical connections need to be made with the guide wire 6" during the replacement operation.

The invention is not limited to the previously described examples. In particular, features of the illustrated examples can be combined together with variations that are not shown.

Other variations and improvements can be provided without necessarily departing from the scope of the invention.

CITED REFERENCES

[1]: *"Registry of Transcatheter Aortic-Valve Implantation in High-Risk Patients"*, Gilard et al; the New England Journal of Medicine: pg. 1705-1715.

[2]: *"Left Ventricular Guidewire Pacing to Simplify Aortic Balloon Valvuloplasty"*, Susanne Navarini et al; Catheterization and Cardiovascular Interventions 73: pg. 426-427 (2009).

[3]: *"A novel Approach for Transcoronary Pacing in a Porcine Model"*, Roland Prodzinsky et al; Journal of Invasive Cardiology 24(9): pg. 451-455 (2012).

[4]: *"Optimizing of Transcoronary Pacing in a Porcine Model"*, Konstantin M. Heinroth, et al, Journal of Invasive Cardiology 21, pg. 634-638 (2009).

The invention claimed is:

1. An assembly for replacing a heart valve by the percutaneous route, comprising:

an introducer comprising at least one tubular introduction sheath intended to be introduced into an artery of a human body (C) and to allow through a surgical intervention device;

at least one bipolar guide wire, intended to be introduced into the tubular introduction sheath and configured to advance an artificial valve intended to replace the heart valve, the bipolar guide wire comprising a metal core coated with an electrically isolating sheath on a central portion between a proximal end and a distal end of the bipolar guide wire, the metal core being non-electrically isolated on the length of the bipolar guide wire beyond the central portion, the electrically isolating sheath comprising an outer periphery and integrating an electrically conductive element, for which a distal portion is apparent towards the exterior on at least one part of an outer periphery of the electrically isolating sheath configured to be in contact with the subcutaneous tissue of the body or with the artery and for which a proximal portion is apparent towards the exterior on the at least one part of the outer periphery of the electrically isolating sheath configured to be accessible from outside the body (C) when the bipolar guide wire is introduced into the tubular introduction sheath, with the proximal portion acting as a connection to an electrode of a cardiac stimulator configured to be outside the body, and the metal core of the bipolar guide wire acts as a connection to another electrode of the cardiac stimulator.

2. The assembly as claimed in claim 1, wherein the electrode of the cardiac stimulator connected to the electrically conductive element integrated in the sheath of the bipolar guide wire is an anode, and the electrode of the cardiac stimulator which is connected to the metal core of the guide wire is a cathode.

3. The assembly as claimed in claim 1, wherein the electrically conductive element is a metal layer embedded in the isolating sheath, except for its distal and proximal portions.

4. The assembly as claimed in claim 1, wherein a distal end of the non-electrically isolated the metal core of the guide wire intended to come into contact with the wall of the left ventricle of the heart of a patient is a portion that is more flexible than the remainder of the guide wire.

5. The assembly as claimed in claim 4, wherein the more flexible portion is adapted to wrap around itself when it comes into contact with the wall of the left ventricle of the heart of a patient.

6. The assembly as claimed in claim 1, wherein a distal portion of the electrically conductive element is connected to an electrical connection, which is intended to be connected to an electrode of a cardiac stimulator configured to be outside the body.

7. An assembly for replacing a heart valve by the percutaneous route, comprising:
   a valve delivery catheter comprising at least one tubular introduction sheath, intended to be introduced into an artery of a human body;
   at least one bipolar guide wire, intended to be introduced into the tubular introduction sheath of the introducer and configured to advance an artificial valve intended to replace the heart valve, the bipolar guide wire comprising a metal core coated with an electrically isolating sheath on a central portion between a proximal end and a distal end of the bipolar guide wire, the metal core being non-electrically isolated on the length of the bipolar guide wire, the electrically isolating sheath comprising an outer periphery and integrating an electrically conductive element, for which a distal portion is apparent on towards the exterior at least one part of the outer periphery of the electrically isolating sheath configured to be in contact with the subcutaneous tissue of the body or with the artery and for which a proximal portion is apparent towards the exterior on at least one part of the outer periphery of the electrically isolating sheath configured to be accessible from outside the body (C) when the bipolar guide wire is introduced into the tubular introduction sheath, with the proximal portion acting as a connection to an electrode of a cardiac stimulator configured to be outside the body, and the metal core of the bipolar guide wire acts as a connection to another electrode of the cardiac stimulator.

* * * * *